(12) United States Patent
Schlenker (10) Patent No.: US 10,271,714 B2
(45) Date of Patent: Apr. 30, 2019

(54) ENDOSCOPE (71) Applicant: Scholly Fiberoptic GmbH, Denzlingen (DE)

(72) Inventor: Stefan Schlenker, Freiburg (DE)

(73) Assignee: SCHOLLY FIBEROPTIC GMBH, Denzlingen (DE)

( * ) Notice: Subject to any disclaimer, the term of this patent is extended or adjusted under 35 U.S.C. 154(b) by 219 days.

(21) Appl. No.: 14/758,356

(22) PCT Filed: May 10, 2013

(86) PCT No.: PCT/EP2013/001388
§ 371 (c)(1),
(2) Date: Jun. 29, 2015

(87) PCT Pub. No.: WO2014/106515
PCT Pub. Date: Jul. 10, 2014

(65) Prior Publication Data
US 2015/0351614 A1  Dec. 10, 2015

(30) Foreign Application Priority Data
Jan. 7, 2013 (DE) .................... 20 2013 000 025 U (51) Int. Cl.
*A61B 1/00* (2006.01)
*A61M 39/10* (2006.01)
*G02B 23/24* (2006.01)
*A61B 1/015* (2006.01)

(52) U.S. Cl.
CPC ...... *A61B 1/00128* (2013.01); *A61B 1/00126* (2013.01); *A61B 1/015* (2013.01); *A61M 39/1011* (2013.01); *G02B 23/2476* (2013.01)

(58) Field of Classification Search
CPC ............ A61B 1/00128; A61B 1/00135; A61B 1/00142
USPC ......................................... 600/121, 125, 104
See application file for complete search history.

(56) References Cited

U.S. PATENT DOCUMENTS

| | | | |
|---|---|---|---|
| 5,368,014 A | 11/1994 | Anapliotis et al. | |
| 5,807,237 A * | 9/1998 | Tindel | A61B 1/313 600/114 |
| 6,129,392 A * | 10/2000 | Dittrich | A61B 1/00128 285/314 |
| 6,682,477 B2 * | 1/2004 | Boebel | A61B 1/00098 600/104 |
| 7,666,170 B2 | 2/2010 | Gual | |

(Continued)

FOREIGN PATENT DOCUMENTS

DE       602006000889       6/2009

*Primary Examiner* — Alexandra L Newton
(74) *Attorney, Agent, or Firm* — Volpe and Koenig, P.C.

(57) ABSTRACT

The invention relates to an endoscope (1), comprising an endoscope tube (3) fastened to a main body (2). According to the invention a connection piece (4), to which a cannula end (6) of a cannula (7) that can be placed onto the endoscope tube (3) can be fastened, is arranged on the endoscope tube (3) in such a way that the connection piece is axially movable between a first position and a second position, wherein a shaped element (8) of the main body (2) and a counter-shaped element (9) of the connection piece (4) form a rotation-prevention mechanism in the first position and enable a rotational motion of the connection piece (4) about a longitudinal axis of the endoscope tube (3) in the second position.

11 Claims, 4 Drawing Sheets

(56) References Cited

U.S. PATENT DOCUMENTS

| | | | |
|---|---|---|---|
| 2003/0055315 A1 | 3/2003 | Gatto et al. | |
| 2005/0085692 A1* | 4/2005 | Kiehn | A61B 1/00105 600/130 |
| 2006/0009677 A1* | 1/2006 | Lehmann | A61B 1/00126 600/104 |
| 2011/0276057 A1* | 11/2011 | Conlon | A61B 17/29 606/130 |

* cited by examiner

ENDOSCOPE

BACKGROUND

The invention relates to an endoscope, comprising a main body, an endoscope tube fixedly connected to the main body, and a connection piece for a cannula that can be placed over the endoscope tube, wherein on the connection piece there is configured a connection to which a cannula end of the cannula can be fastened.

Endoscopes of this type are known and have proved of value for conveying with the cannula, for instance, liquids out of or into a cavity examined with the endoscope tube.

In this context, on the cannula end are frequently configured laterally protruding connection branches, which prevent the cannula ends from being able to be fastened in any chosen orientation to the main body. On the other hand, the orientation in which the cannula end can be fastened to the main body is predetermined by the respective connection.

DE 60 2006 000 889 T2 discloses a medical valve connection having a Luer lock connecting piece, wherein on the connecting piece are configured spring claws, which engage in complementarily shaped teeth in order to define a locking apparatus which acts only in one direction and which is designed to permit rotation of the connecting piece in relation to a body only in a single rotational direction in order to enable release of a Luer lock connecting piece which is screwed on.

SUMMARY

The object of the invention is to provide an endoscope in which a fastening of the cannula end in an undesirable orientation is avoidable.

In order to achieve this object, one or more features of the invention are provided. In particular, it is thus proposed according to the invention that the connection piece is arranged along a longitudinal axis of the endoscope tube such that it is displaceable in relation to the main body between a first position and a second position, that on the main body there is configured a shaped element, that on the connection piece there is configured a counter-shaped element corresponding to the shaped element, that the shaped element and the counter-shaped element in the first position mutually engage and lock the connection piece against a rotary motion about the longitudinal axis, and that the shaped element and the counter-shaped element in the second position are arranged at a distance apart and enable a rotary motion of the connection piece relative to the main body about the longitudinal axis. Thus the connection piece with the thereto fastened cannula end can in the second position be oriented according to choice by a suitable rotary motion in order to avoid undesirable orientations of the cannula end on the main body. In the first position, the cannula end is fixed against rotary motion, so that the undesirable orientations of the cannula end cannot be inadvertently readopted after the alignment. The first position, in which the locking against rotary motions is active, thus constitutes a usage position of the endoscope. The second position, in which the aforementioned locking is inactive and the counter-shaped element is disengaged from the shaped element, thus constitutes a preparatory state for the actual use of the endoscope. Since, in the second position, the shaped element and the counter-shaped element are arranged at a distance apart, a rotary motion in both rotational directions about the longitudinal axis is enabled. The desired orientation can hence be rapidly achieved. In addition, an alignment of the cannula end in relation to the main body is possible without twisting or rotation of the cannula.

In one embodiment of the invention, it can be provided that a restoring element there is configured, which restoring element subjects the connection piece to a restoring force which transfers the connection piece into the first position. It is here of advantage that the first position can be automatically adopted as soon as the connection piece is released by the user. It is thus possible to achieve in a simple manner that the aforementioned usage position is adopted automatically.

For instance, it can here be provided that the restoring element has a spring. It is here particularly favorable if the restoring element has a helical spring. A mechanical restoring force can thus be applied to the connection piece.

Alternatively or additionally, it can be provided that the restoring element has at least one magnet. It is here of advantage that a magnetic restoring force can be developed. For instance, the restoring element can have a pair of like-poled or oppositely-poled magnets. A repelling or an attracting restoring force can thus be developed.

In one embodiment of the invention, it can be provided that the connection has a screw thread. For instance, the connection can be configured as part of a Luer lock system. It is here of advantage that a rapid and secure fastening of the cannula end is realizable or attainable.

In one embodiment of the invention, it can be provided that the shaped element has a succession of recesses and elevations in the peripheral direction. It is here of advantage that the recesses and elevations can define with the counter-shaped element a form closure, which produces a rotary locking.

Alternatively or additionally, it can here be provided that the counter-shaped element has a succession of recesses and elevations in the peripheral direction. If the recesses and elevations of the counter-shaped element are configured complementary to the recesses and elevations of the shaped element, then the mentioned form closure can be established in a particularly simple manner.

For instance, it can here be provided that the recesses and elevations on the shaped element are configured radially on the outside. The recesses and elevations of the counter-shaped element can in this case be configured on the counter-shaped element radially on the inside. The counter-shaped element can thus overlap the shaped element radially on the outside, wherein the recesses and elevations of the counter-shaped element interact with the recesses and elevations of the shaped element.

However, the converse arrangement, in which the shaped element has radially on the inside a succession of recesses and elevations in the peripheral direction and the counter-shaped element has radially on the outside a succession of recesses and elevations in the peripheral direction, wherein the shaped element embraces the counter-shaped element radially on the outside, is also advantageously usable.

In one embodiment of the invention, it can be provided that the shaped element and/or the counter-shaped element has/have an n-fold rotational symmetry, wherein n is greater than or equal to four. By an n-fold rotational symmetry is here understood a rotational symmetry which, upon a coverage through $1/_n$ of a complete revolution, automatically causes the respective body to rotate upon itself. It is here of advantage that at least four orientations are defined, in which the cannula end can be aligned in relation to the main body and can be fixed against rotary motions. It is particularly favorable if the rotational symmetry of the shaped element and/or of the counter-shaped element is large in order to define a greatest possible number of adoptable orientations. For instance, the rotational symmetry can be n-fold, with n greater than or equal to 10. It is particularly favorable if the shaped element and the counter-shaped element are configured complementary to each other and thus have the same rotational symmetry.

In one embodiment of the invention, it can be provided that on the cannula end there is configured at least one laterally protruding connection branch, which opens out into the cannula end. It is here of advantage that lateral feeds into the cannula are provided. The invention enables the position of the connection branch on the main body after fastening of the cannula end to be chosen according to requirement or corrected.

It is particularly favorable if on the cannula end are configured two connection branches, which protrude laterally on opposite sides and which respectively open out into a channel in the cannula. Thus, a simultaneous liquid supply and liquid removal through the cannula is realizable for instance.

In one embodiment of the invention, it can be provided that on the main body there is configured at least one laterally protruding light-carrying connection branch for the connection of a fiber-optic light guide or of a light source, or another further connection branch. It is here of advantage that light for the examination of a hollow body with the endoscope can be introduced into the cavity. Preferably, the endoscope tube has for this purpose a fiber-optic light guide.

In one embodiment of the invention, it can be provided that on the main body there is configured at least one access opening to an interior of the endoscope tube. It is here of advantage that the endoscope tube is easily accessible. It is particularly favorable if the access opening is axially oriented to allow the endoscope tube to be reached without any bends.

In one embodiment of the invention, it can be provided that on the main body and/or the connection piece is provided a guide element for guiding an axial motion of the connection piece. It is here of advantage that the motion between the first position and the second position is guidable in a defined manner.

In one embodiment of the invention, it can be provided that on the main body and/or the connection piece there is configured a stop element for limiting the or an axial motion of the connection piece. It is here of advantage that the first position and/or the second position is/are definable by the position of the stop elements. Excessive pulling apart of the connection piece and the main body can thus be avoided.

BRIEF DESCRIPTION OF THE DRAWINGS

The invention is now explained in greater detail with reference to illustrative embodiments, yet is not limited to these illustrative embodiments. Further illustrative embodiments are obtained by mutually combining the features of individual or a plurality of claims and/or with individual features or a plurality of features, wherein:

DETAILED DESCRIPTION OF THE PREFERRED EMBODIMENTS

Figure 1:
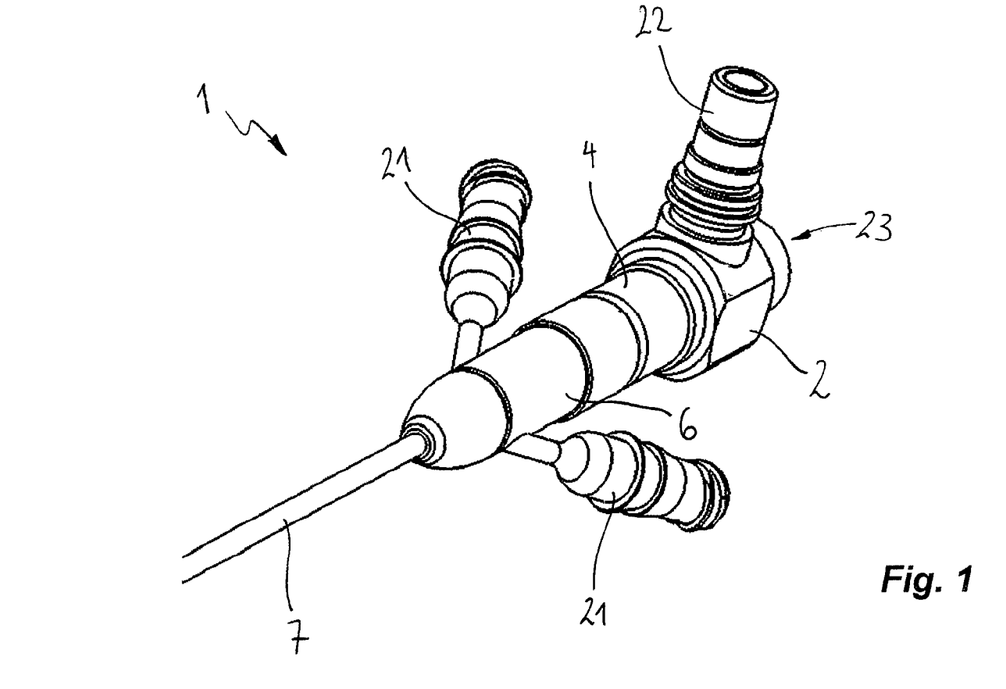
FIG. 1 shows an endoscope according to the invention with mounted cannula.

FIG. 1 shows in a three-dimensional perspective view an endoscope according to the invention, denoted in its entirety by 1.

The endoscope 1 has a main body 2. The main body 2 can be of multipart or—as indicated here—of single-part configuration.

Figure 2:
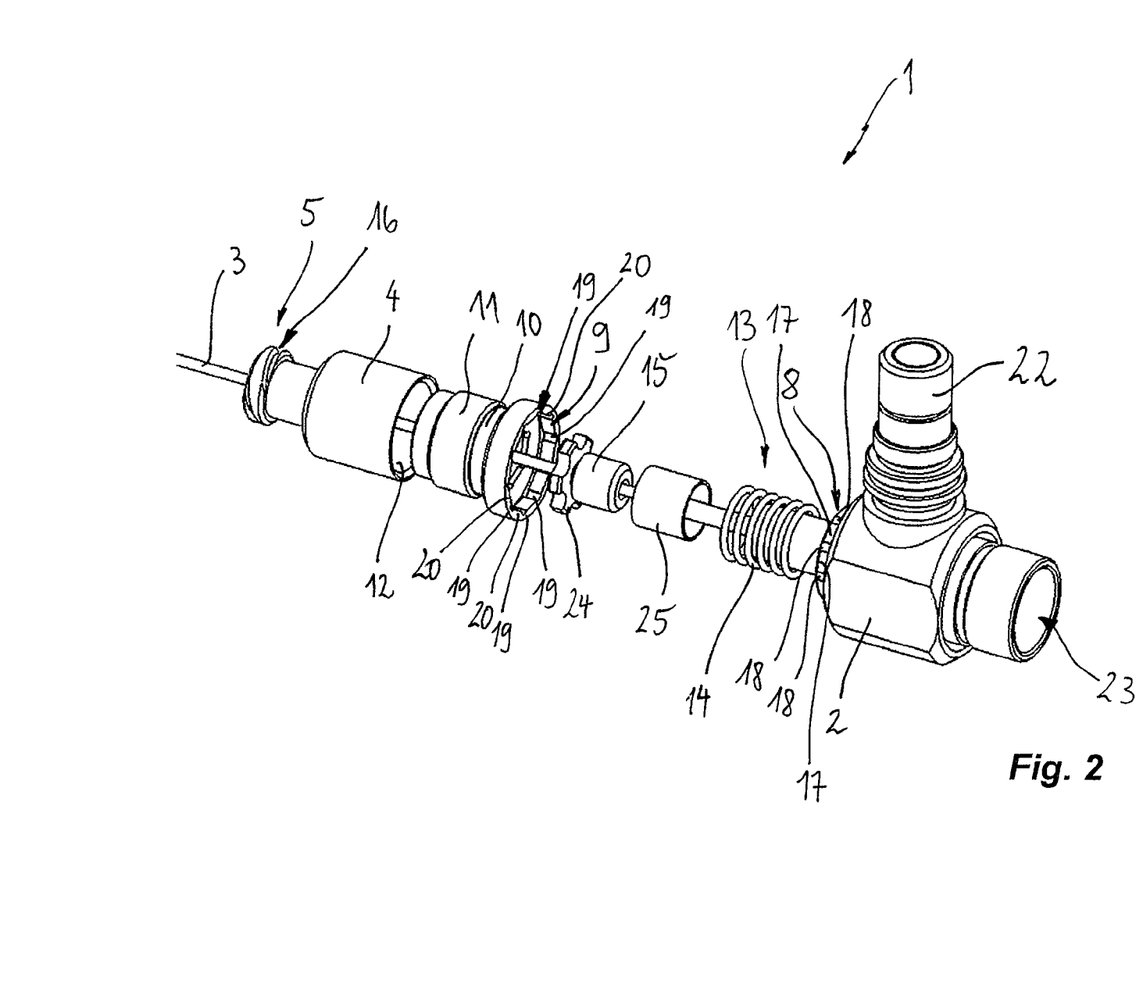
FIG. 2 shows the endoscope according to FIG. 1 in exploded representation, with cannula removed.

On the main body 2 is arranged an endoscope tube 3, which can be seen more closely in FIG. 2. The endoscope tube is fixedly connected to the main body 2.

On the endoscope 1 there is configured a connection piece 4. The connection piece 4 has a connection 5, which can be seen in FIG. 2.

The connection 5 is configured and set up for the fastening of a cannula end 6 of a cannula 7. For the fastening of the cannula end 6 to the connection 5, the cannula end 6, with the cannula 7, is placed or pulled over the endoscope tube 3 in a known manner.

In FIG. 2 it can be seen that on the main body 2 there is configured a shaped element 8.

In the illustrative embodiment according to FIGS. 1 and 2, the shaped element 8 is configured integrally on the main body 2. In further illustrative embodiments, the main body 2 is of multipart construction and the shaped element 8 is configured as a separate part of the main body 2.

On the connection piece 4 there is configured a counter-shaped element 9.

In the illustrative embodiment according to FIGS. 1 and 2, the counter-shaped element 9 is configured for this purpose on a separate sleeve 10, which has an external thread 11 with which the sleeve 10 is screwed into a fitting internal thread 12 of the connection piece 4. In further illustrative embodiments, the counter-shaped element 9 is formed integrally onto the connection piece 4.

The counter-shaped element 9 has an internal contour, which fits with an external contour of the shaped element 8, so that the counter-shaped element 9 is configured correspondingly to the shaped element 8.

From the representation in FIG. 2, it can be seen that the connection piece 4 is arranged along a longitudinal axis of the endoscope tube 3 such that is axially displaceable relative to the main body 2.

In this context, FIG. 1 shows a first position, in which the counter-shaped element 9 interacts with the shaped element 8 such that the shaped element 8 and the counter-shaped element 9 mutually engage.

In this first position, a rotary motion of the connection piece 4 about the mentioned longitudinal axis of the endoscope tube 3 is prevented, so that the rotary motion is locked.

Throughout the description, the terms "axially" and "radially", and the term "in the peripheral direction" are used in relation to the longitudinal axis of the endoscope tube 3.

The connection piece 4 with its counter-shaped element 9 is not fixedly connected to the main body 2 and its shaped element 8, but rather the connection piece 4 can be moved away from the main body 2 by an axial displacement and transferred into a second position.

In this second position, the shaped element 8 and the counter-shaped element 9 are at an axial distance apart. The rotary motion of the connection piece 4 relative to the main body 2 about the longitudinal axis of the endoscope tube 3 is thus enabled in both rotational directions.

The connection piece 4 can thus be aligned in a desired orientation in relation to the main body 2 by rotation in the second position.

The endoscope 1 has a restoring element 13, which subjects the connection piece 4 to a restoring force in such a way that the connection piece 4 is automatically returned into the first position.

In the illustrative embodiment according to FIGS. 1 and 2, this restoring element 13 is configured as a spring 14 in order to develop a mechanical restoring force.

The spring 14 is herein supported on a retaining element 15. The retaining element 15 is fastened to the main body 2, for instance screwed into this.

In the usage position, the spring 14, with its end facing away from the retaining element 15, acts upon the counter-shaped element 9.

In FIG. 2 it can be seen that the connection 5 is configured as part of a Luer lock system and has a screw thread 16.

The complete locking against rotary motions in the first position has the advantage that the cannula end 6 can be screwed onto the connection 5 and unscrewed from this same without the connection piece 4 being accidentally twisted in relation to the main body 2.

From FIG. 2, it can be seen that the shaped element 8 has a succession of recesses 17 and elevations 18.

Recesses 17 and elevations 18 herein follow alternately one upon the other in the peripheral direction of the shaped element 8.

Complementary hereto, the counter-shaped element 9 has recesses 19 and elevations 20.

The recesses 19 and elevations 20 likewise alternate in the peripheral direction.

The shaped element 8 here has precisely as many recesses 17 as the counter-shaped element 9 has elevations.

Conversely, the counter-shaped element 9 has just as many recesses 19 as the shaped element 8 has elevations.

The recesses 17 are matched to the elevations 20 and the recesses 19 are matched to the elevations 18 such that the counter-shaped element 9 and the shaped element 8 positively interlock in the first position.

From FIG. 2 it can be seen that the counter-shaped element 9 has ten regularly arranged recesses 19 and just as many regularly arranged elevations 20. The counter-shaped element 9 thus has 10-fold rotational symmetry. The shaped element 8 has exactly the same rotational symmetry.

In the illustrative embodiment according to FIG. 1 and FIG. 2, the recesses 17 and elevations 18 on the shaped element 8 are arranged radially on the outside, while the recesses 19 and elevations 20 on the counter-shaped element 9 are arranged radially on the inside.

In the first position, the counter-shaped element 9 thus overlaps the shaped element 8 radially on the outside.

In further illustrative embodiments, the inverted arrangement, in which the counter-shaped element 9 engages in the shaped element 8, is realized.

On the cannula end 6 are configured two connection branches 21.

The connection branches 21 protrude laterally from the endoscope 1 in relation to the longitudinal axis of the endoscope tube 3.

In a manner which is known per se, each of the connection branches 21 is connected to a longitudinal channel (not further represented) in the cannula 7. The connection branches 21 thus open out into the cannula end 6 in such a way that, through each of the two connection branches 21, substances can be conveyed separately from each other out of or into the examined cavity.

On the main body 2 is further configured a light-carrying connection branch 22.

The light-carrying connection branch 22 protrudes laterally from the main body 2 in relation to the longitudinal axis of the endoscope tube 3.

As a result of the rotary motion of the connection piece 4 in the second position, the position of the light-carrying connection branch 22 in relation to the connection branches 21 can thus be freely chosen according to requirement, so that the branches 21, 22 do not interfere with each other.

In particular, a situation in which the connection branches 21 and the light-carrying connection branches 22 lie in a common plane can thus be avoided.

In a manner which is known per se, a fiber-optic light guide or a light source (not further represented) can be connected to the light-carrying connection branches 22 in order to conduct light into the endoscope tube 3 and, with the latter, into the cavity to be examined.

On the main body 2 is finally configured an axially oriented access opening 23, through which an interior of the endoscope tube 3 is accessible.

In FIG. 2 it is also evident that on the retaining element 15 are configured guide elements 24 in the form of radial projections, with which the axial motion of the connection piece 4 between the first position and the second position is guided.

A sleeve-shaped stop element 25 serves to limit this axial motion and thus defines the second position.

Figure 3:
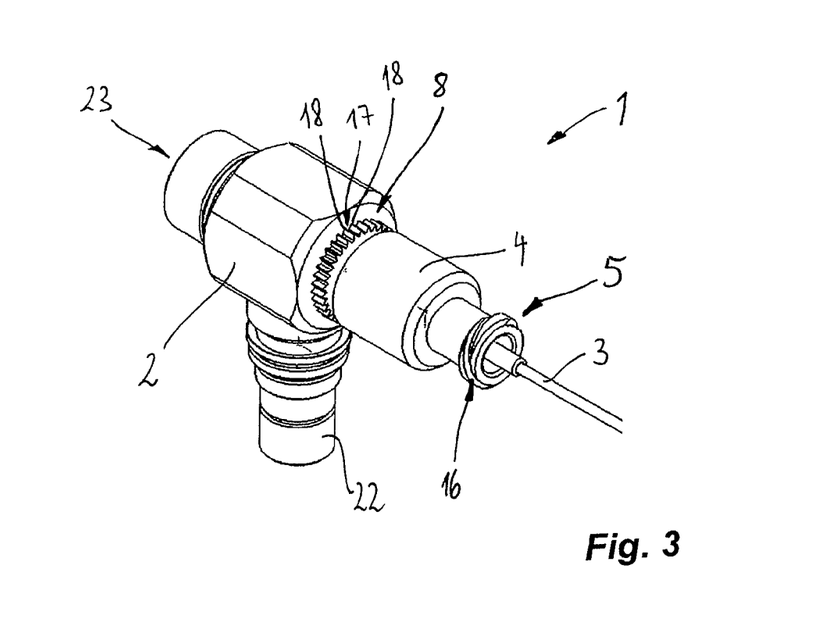
FIG. 3 shows a further endoscope according to the invention with a connection piece located in the second position.
Figure 4:
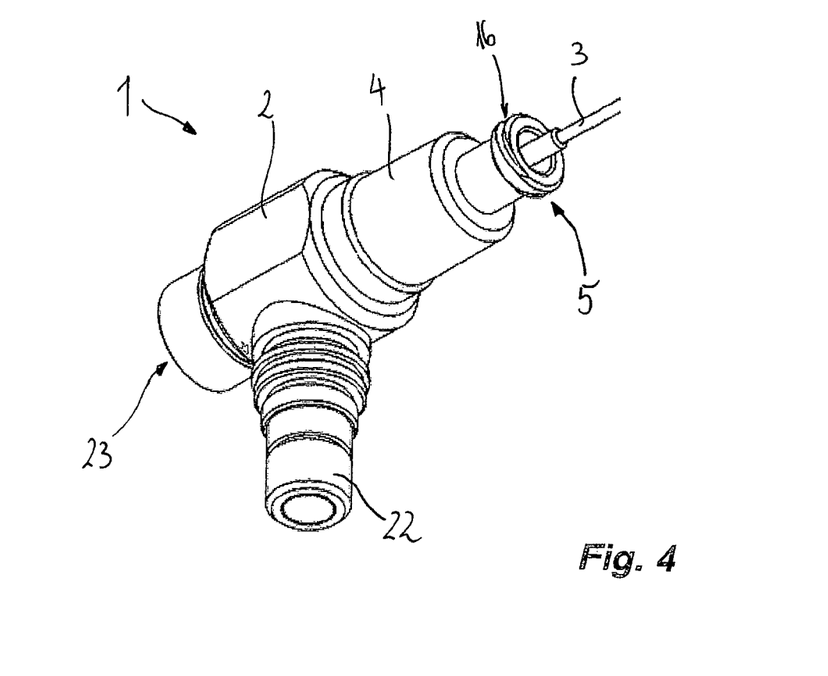
FIG. 4 shows the endoscope according to FIG. 3 with a connection piece located in the first position.

FIG. 3 and FIG. 4 show in three-dimensional oblique views a second endoscope 1 according to the invention.

In the representations in FIG. 3 and FIG. 4, components which in function and/or design are of the same type as or similar to the illustrative embodiment according to FIGS. 1 and 2 are denoted by the same reference symbols and are not described separately all over again. The statements relating to FIG. 1 and FIG. 2 thus apply correspondingly to FIG. 3 and FIG. 4.

FIG. 3 here shows the second position, in which the connection piece 4 with the counter-shaped element 9 (not further visible) is removed from the shaped element 8. A rotation about the longitudinal axis of the endoscope tube 3 is thus enabled.

By contrast, FIG. 4 shows the situation in which the connection piece 4 is in the first position. The connection piece 4 is thus fixed against rotations about the axis of the endoscope tube 3.

In the illustrative embodiment according to FIG. 3 and FIG. 4, the shaped element 8 is configured as an external toothing, wherein the teeth define elevations 18 and the tooth spaces define recesses 17.

The shaped element 8 thus has a higher discrete rotational symmetry compared to the illustrative embodiment according to FIG. 1 and FIG. 2. The counter-shaped element 9 (not further represented) is correspondingly configured with a fitting internal toothing.

Figure 5:
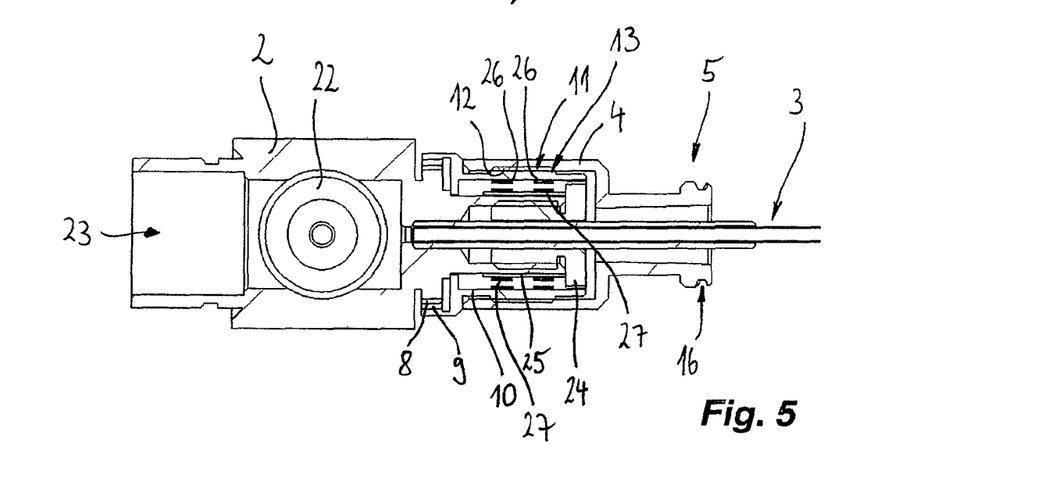
FIG. 5 shows a further endoscope according to the invention in a simplified sectional representation with a restoring element having magnets.

FIG. 5 shows an axial sectional representation of a further endoscope 1 according to the invention. In the representation according to FIG. 5, components which in design and/or function are of the same type as or similar to the illustrative embodiments according to FIGS. 1 to 4 are again denoted by the same reference symbols and are not described separately all over again. The statements relating to FIG. 1 to FIG. 4 therefore apply correspondingly to FIG. 5.

In the illustrative embodiment according to FIG. 5, the restoring element 13 has annular magnets 26, which interact with annular magnets 27 on the main body 2.

The magnets 26 are here poled oppositely to the magnets 27 in order to bring the connection piece 4 into the first position shown in FIG. 5. The magnets 26 are arranged concentrically to the magnets 27.

Figure 6:
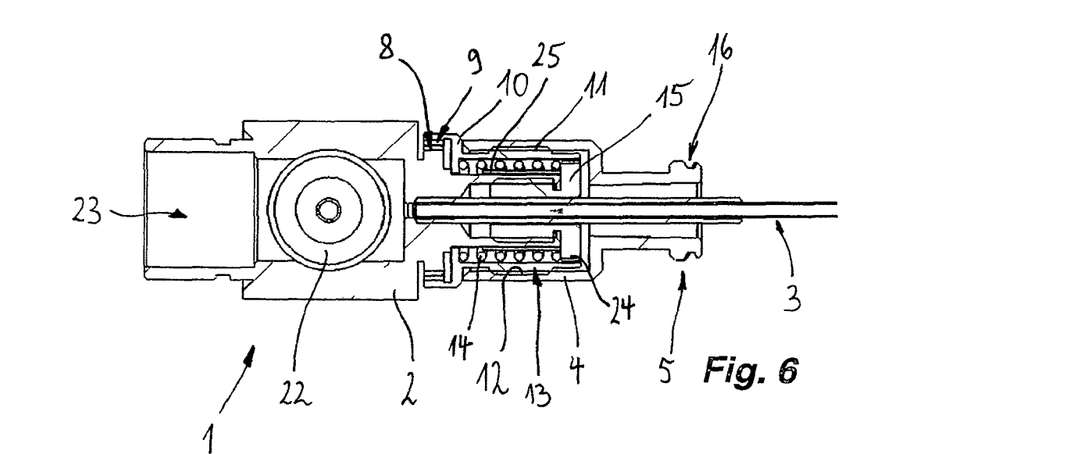
FIG. 6 shows a further endoscope according to the invention in simplified sectional representation with a restoring element having a helical spring.

FIG. 6 shows a simplified axial section through a further endoscope 1 according to the invention. In FIG. 6, components which in design and/or function are of the same type as or similar to the illustrative embodiments according to FIG. 1 to FIG. 5 are again denoted by the same reference symbols and are not described separately all over again. The statements relating to the illustrative embodiments according to FIG. 1 and FIG. 5 thus apply correspondingly to FIG. 6.

FIG. 6 can thus be regarded as an assembly drawing of the arrangement according to FIG. 2.

In FIG. 6 it can be seen that the restoring element 13 returns the connection piece 4 into the first position, in which the shaped element 8 and the counter-shaped element 9 mutually engage. For this purpose, the spring 14 is supported with one axial end on the sleeve 10 and with the other axial end against the retaining element 15.

It can further be seen that the retaining element 15 is screwed into the main body 2.

The guide elements 24 guide the axial motion of the connection piece 4 with the screwed-in sleeve 10 relative to the main body 2 between the first position and the second position.

From the represented illustrative embodiments it can be seen that the restoring elements 13 are respectively aligned concentrically in relation to the endoscope tube 3. This is favorable in order to develop a concentric restoring force.

In the case of an endoscope 1 comprising an endoscope tube 3 fastened to a main body 2, it is proposed to arrange a connection piece 4, to which a cannula end 6 of a cannula 7 placeable on the endoscope tube 3 can be fastened, such that it is axially displaceable between a first position and a second position on the endoscope tube 3, wherein a shaped element 8 of the main body 2 and a counter-shaped element 9 of the connection piece 4 form a twist prevention mechanism in the first position and enable a rotary motion of the connection piece 4 about a longitudinal axis of the endoscope tube 3 in the second position.

The invention claimed is:

1. An endoscope (1), comprising:
a main body (2),
an endoscope tube (3) fixedly connected to the main body (2),
a connection piece (4) for a cannula (7) that is placed over the endoscope tube (3), a connection (5) on the connection piece (4) to which a cannula end (6) of the cannula (7) is fastenable, the connection piece (4) is arranged along a longitudinal axis of the endoscope tube (3) to be axially displaceable in relation to the main body (2) between a first position and a second position,
a restoring element (13), associated with the connection piece (4), which subjects the connection piece (4) to an axially directed restoring force which axially transfers the connection piece (4) into the first position, a shaped element (8) is provided on the main body (2), the shaped element (8) having a succession of recesses (17) and elevations (18) radially arranged on an outside portion thereof; a counter-shaped element (9) is provided on the connection piece (4), the counter-shaped element (9) corresponding to the shaped element (8), the counter-shaped element (9) has a succession of recesses (19) and elevations (20) in the peripheral direction arranged radially on an inside of the counter-shaped element, wherein the counter-shaped element is configured to overlap the shaped element radially on the outside, the recesses and elevations of the counter-shaped element interact with the elevations and recesses of the shaped element; the shaped element (8) and the counter-shaped element (9) in the first position mutually engage and lock the connection piece (4) against a rotary motion about the longitudinal axis, and the shaped element (8) and the counter-shaped element (9) in the second position are arranged axially spaced apart and enable a rotary motion of the connection piece (4) relative to the main body (2) about the longitudinal axis to one of a plurality of rotary adjustment positions of the connection piece (4) relative to the main body (2).

2. The endoscope (1) as claimed in claim 1, wherein the restoring element (13) comprises a spring (14).

3. The endoscope (1) as claimed in claim 1, wherein the restoring element (13) has at least one magnet (26, 27).

4. The endoscope (1) as claimed in claim 1, wherein the connection (5) has a screw thread (16).

5. The endoscope (1) as claimed in claim 1, wherein the shaped element (8) or the counter-shaped element (9) has an n-fold rotational symmetry, wherein n is greater than or equal to four.

6. The endoscope (1) as claimed in claim 1, wherein on the cannula end (6) there is configured at least one laterally protruding connection branch (21), which opens out into the cannula end (6).

7. The endoscope (1) as claimed in claim 1, wherein on the main body (2) there is configured at least one laterally protruding light-carrying connection branch (22) for connection of a fiber-optic light guide or of a light source.

8. The endoscope (1) as claimed in claim 1, wherein on the main body (2) there is at least one access opening (23) to an interior of the endoscope tube (3).

9. The endoscope (1) as claimed in claim 1, wherein at least one of on the main body (2) or the connection piece (4) there is at least one guide element (24) for guiding an axial motion of the connection piece (4), or at least one stop element (25) for limiting the axial motion of the connection piece (4).

10. The endoscope (1) as claimed in claim 1, wherein at least one of on the main body (2) or the connection piece (4) there is at least one guide element (24) for guiding an axial motion of the connection piece (4), and at least one stop element (25) for limiting the axial motion of the connection piece (4).

11. An endoscope (1), comprising:
a main body (2),
an endoscope tube (3) fixedly connected to the main body (2),
a connection piece (4) for a cannula (7) that is placed over the endoscope tube (3), a connection (5) on the connection piece (4) to which a cannula end (6) of the cannula (7) is fastenable, the connection piece (4) is arranged along a longitudinal axis of the endoscope tube (3) to be axially displaceable in relation to the main body (2) between a first position and a second position, a restoring element (13), associated with the connection piece (4), which subjects the connection piece (4) to an axially directed restoring force which axially transfers the connection piece (4) into the first position, a shaped element (8) is provided on the main body (2), the shaped element (8) having a succession of recesses (17) and elevations (18) radially arranged on an inside portion thereof; a counter-shaped element (9) is provided on the connection piece (4), the counter-shaped element (9) corresponding to the shaped element (8), the counter-shaped element (9) has a succession of recesses (19) and elevations (20) in the peripheral direction arranged radially on an outside of the counter-shaped element wherein the shaped element is configured to overlap the counter-shaped element radially on the outside, the recesses and elevations of the counter-shaped element interact with the elevations and recesses of the shaped element; the shaped element (8) and the counter-shaped element (9) in the first position mutually engage and lock the connection piece (4) against a rotary motion about the longitudinal axis, and the shaped element (8) and the counter-shaped element (9) in the second position are arranged axially spaced apart and enable a rotary motion of the connection piece (4) relative to the main body (2) about the longitudinal axis to one of a plurality of rotary adjustment positions of the connection piece (4) relative to the main body (2).

\* \* \* \* \*